(12) United States Patent
Ostrovsky et al.

(10) Patent No.: US 9,504,553 B2
(45) Date of Patent: *Nov. 29, 2016

(54) URETERAL STENT

(71) Applicant: Boston Scientific Scimed, Inc., Maple Grove, MN (US)

(72) Inventors: Isaac Ostrovsky, Wellesley, MA (US); Jozef Slanda, Milford, MA (US); Jianmin Li, Lexington, MA (US); Hamid Davoudi, Westwood, MA (US); Robert T. Miragliuolo, Chelmsford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/722,844

(22) Filed: May 27, 2015

(65) Prior Publication Data

US 2015/0250581 A1 Sep. 10, 2015

Related U.S. Application Data

(63) Continuation of application No. 13/965,867, filed on Aug. 13, 2013, now Pat. No. 9,066,823, which is a continuation of application No. 12/635,345, filed on Dec. 10, 2009, now Pat. No. 8,512,272.

(60) Provisional application No. 61/139,966, filed on Dec. 22, 2008.

(51) Int. Cl.
*A61M 5/00* (2006.01)
*A61F 2/04* (2013.01)
(Continued)

(52) U.S. Cl.
CPC .................. *A61F 2/042* (2013.01); *A61F 2/82* (2013.01); *A61L 31/128* (2013.01); *A61M 25/00* (2013.01); *A61M 27/008* (2013.01)

(58) Field of Classification Search
CPC ..... A61M 25/00; A61M 27/008; A61F 2/82; A61F 2/042; A61L 31/128
See application file for complete search history.

(56) References Cited

U.S. PATENT DOCUMENTS

| 4,671,795 A | 6/1987 | Mulchin |
| 4,820,262 A | 4/1989 | Finney |

(Continued)

FOREIGN PATENT DOCUMENTS

| WO | 00/66032 | 11/2000 |
| WO | 03/075795 A1 | 9/2003 |

(Continued)

OTHER PUBLICATIONS

"Contour VL Variable Length Percuflex Stents with Hydroplus Coating", Boston Scientific Corporation, Technical Information, Copyright 2002, retrieved from www.bostonscientific.com, 1 page.

(Continued)

*Primary Examiner* — Philip R Wiest

(57) ABSTRACT

In some embodiments, a ureteral stent includes an elongate member having a first portion and a second portion, which is coupled to the first portion. The first portion of the elongate member is configured to be disposed within a kidney of a patient. The second portion of the elongate member, which has a sidewall that defines a lumen, is configured to deliver fluid from a first location of the sidewall of the second portion to a second location of the sidewall of the second portion via capillary action. The second portion of the elongate member is configured to be disposed within at least one of a bladder and a ureter of the patient.

20 Claims, 11 Drawing Sheets

(51) Int. Cl.
  *A61L 31/12* (2006.01)
  *A61M 25/00* (2006.01)
  *A61M 27/00* (2006.01)
  *A61F 2/82* (2013.01)

(56) References Cited

U.S. PATENT DOCUMENTS

| | | | |
|---|---|---|---|
| 4,876,126 A | 10/1989 | Takemura et al. |
| 4,925,445 A | 5/1990 | Sakamoto et al. |
| 4,931,037 A | 6/1990 | Wetterman |
| 5,059,169 A | 10/1991 | Zilber |
| 5,141,502 A | 8/1992 | Macaluso |
| 5,176,626 A | 1/1993 | Soehendra |
| 5,234,456 A | 8/1993 | Silvestrini |
| 5,242,428 A | 9/1993 | Palestrant |
| 5,334,166 A | 8/1994 | Palestrant |
| 5,401,257 A | 3/1995 | Chevalier, Jr. |
| 5,599,291 A | 2/1997 | Balbierz et al. |
| 5,647,843 A | 7/1997 | Mesrobian et al. |
| 5,772,640 A | 6/1998 | Modak et al. |
| 6,332,892 B1 | 12/2001 | Desmond et al. |
| 6,582,472 B2 | 6/2003 | Hart |
| 6,620,202 B2 | 9/2003 | Bottcher et al. |
| 6,656,146 B1 | 12/2003 | Clayman et al. |
| 6,676,623 B2 | 1/2004 | Whitmore |
| 6,676,624 B2 | 1/2004 | Gellman |
| 6,719,804 B2 | 4/2004 | St. Pierre |
| 6,764,519 B2 | 7/2004 | Whitmore, III |
| 6,908,447 B2 | 6/2005 | McWeeney et al. |
| 6,913,625 B2 | 7/2005 | Segura et al. |
| 6,929,664 B2 | 8/2005 | Kolb |
| 6,945,950 B2 | 9/2005 | Clayman et al. |
| 6,991,614 B2 | 1/2006 | McWeeney et al. |
| 7,037,345 B2 | 5/2006 | Bottcher et al. |
| 7,041,139 B2 | 5/2006 | Bluni et al. |
| 7,217,250 B2 | 5/2007 | Kolb |
| 7,291,180 B2 | 11/2007 | St. Pierre |
| 7,316,663 B2 | 1/2008 | Whitmore, III |
| 7,713,308 B2 | 5/2010 | Amos et al. |
| 8,192,500 B2 | 6/2012 | Chung |
| 8,512,272 B2 * | 8/2013 | Ostrovsky ............ A61L 31/128 604/8 |
| 9,066,823 B2 * | 6/2015 | Ostrovsky ............ A61L 31/128 |
| 2002/0055787 A1 | 5/2002 | Lennox et al. |
| 2003/0163204 A1 | 8/2003 | Rix |
| 2003/0171708 A1 | 9/2003 | Segura et al. |
| 2003/0199805 A1 | 10/2003 | McWeeney |
| 2004/0092857 A1 | 5/2004 | Clayman et al. |
| 2004/0127996 A1 | 7/2004 | Reever |
| 2004/0193092 A1 | 9/2004 | Deal |
| 2006/0264912 A1 | 11/2006 | McIntyre et al. |
| 2006/0271202 A1 | 11/2006 | Ward |
| 2008/0077250 A1 | 3/2008 | Amos |
| 2010/0152861 A1 | 6/2010 | Chung |
| 2010/0160848 A1 | 6/2010 | Ostrovsky et al. |
| 2013/0331948 A1 | 12/2013 | Ostrovsky et al. |

FOREIGN PATENT DOCUMENTS

| | | |
|---|---|---|
| WO | 2010/075214 A1 | 7/2010 |
| WO | 00/51521 A1 | 9/2010 |

OTHER PUBLICATIONS

"For Ureteral Access, Passage, and Reduced Trauma", Glidewire Guidewires, Boston Scientific, Technical Information, copyright 2004, retrieved from www.bostonscientific.com/urology, 4 pages.

Denstedt, "Advances in Ureteral Stent Design", CP900, Renal Stone Disease, 1st Annual International Urolithiasis Research Symposium, Jul. 23, 2007, 6 pages.

International Search Report and Written Opinion for PCT Patent Application No. PCT/US2009/068746, mailed on Mar. 31, 2010, 13 pages.

International Preliminary Report on Patentability for International Application No. PCT/US2009/068746, mailed Jul. 7, 2011, 7 pages.

\* cited by examiner

URETERAL STENT

CROSS-REFERENCE TO RELATED APPLICATIONS

This application is a continuation of U.S. patent application Ser. No. 13/965,867, filed on Aug. 13, 2013, entitled "URETERAL STENT", which is a continuation of, and claims priority to, U.S. application Ser. No. 12/635,345, filed on Dec. 10, 2009, entitled "URETERAL STENT", now U.S. Pat. No. 8,512,272, which claims priority to U.S. Provisional Application No. 61/139,966, filed on Dec. 22, 2008, entitled "URETERAL STENT", the disclosures of which are incorporated by reference herein in their entirety.

BACKGROUND

The disclosed invention relates generally to a medical device and more particularly to a ureteral stent having wicking properties.

Ureteral stents are typically placed within a urinary tract of a patient such that one end portion of the ureteral stent is located in a kidney of the patient and the other end portion of the ureteral stent is located in either a bladder or a ureter of the patient. In this manner, fluid from the kidney of the patient can be drained into the bladder of the patient via a lumen of the ureteral stent. Known ureteral stents are typically positioned within the urinary tract of the patient by placing a guidewire within the patient, sliding the ureteral stent on the guidewire, and then pushing the ureteral stent along the guidewire into a desired position using a push rod.

Known ureteral stents are designed to provide optimal functionality while minimizing patient discomfort. Some design features may provide improved comfort but may also decrease functionality. For example, hard stents are known to be more resistant to deformation and easier to position within the urinary tract than soft stents. As the hardness of the stent increases, however, the patient will generally experience greater discomfort while the stent is disposed within the urinary tract. Conversely, softer stents may alleviate patient discomfort, but they are generally more difficult to insert and more susceptible to deformation once inserted into the patient.

Thus, a need exists for ureteral stents that have improved comfort without decreasing the functionality of the stent. For example, a need exists for a soft or otherwise flexible ureteral stent that includes wicking properties. Additionally, a need exists for a method of inserting such ureteral stents within the body.

SUMMARY

Ureteral stents are described herein. In some embodiments, a ureteral stent includes an elongate member having a first portion and a second portion, which is coupled to the first portion. The first portion of the elongate member is configured to be disposed within a kidney of a patient. The second portion of the elongate member, which has a sidewall that defines a lumen, is configured to deliver fluid from a first location of the sidewall of the second portion to a second location of the sidewall of the second portion via capillary action. The second portion of the elongate member is configured to be disposed within at least one of a bladder and a ureter of the patient.

DETAILED DESCRIPTION

In some embodiments, a ureteral stent includes an elongate member having a first portion and a second portion, which is coupled to the first portion. The first portion of the elongate member is configured to be disposed within a kidney or renal pelvis of a patient. The second portion of the elongate member, which has a sidewall that defines a lumen, is configured to deliver fluid from a first location of the sidewall of the second portion to a second location of the sidewall of the second portion via capillary action and/or wicking. The second portion of the elongate member is configured to be disposed within at least one of a bladder and a ureter of the patient.

As used in this specification, the words "proximal" and "distal" refer to the renal pelvis or kidney end and the bladder end of the stent, respectively.

Figure 1:
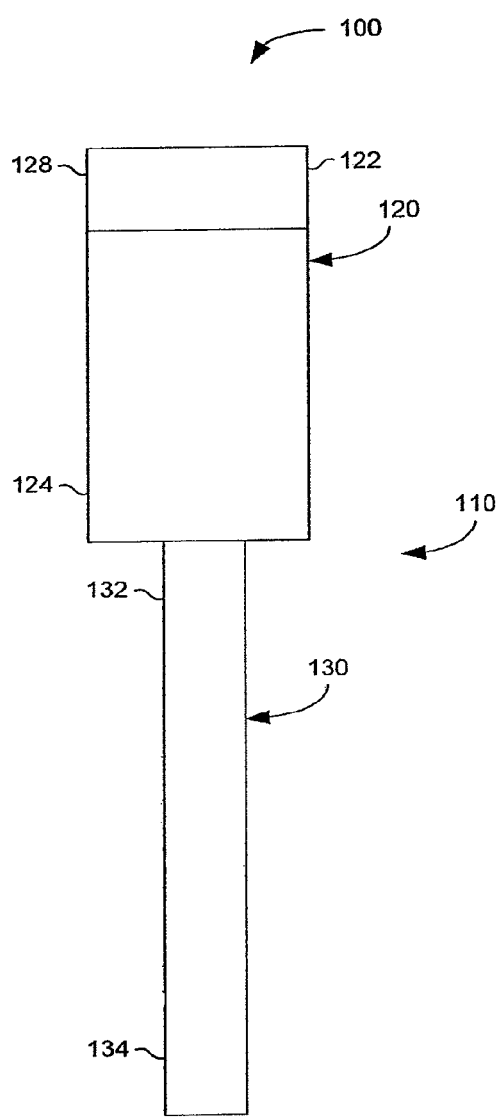
FIG. 1 is a schematic illustration of a ureteral stent according to an embodiment.

FIG. 1 is a schematic illustration of a ureteral stent 100 according to an embodiment of the invention. The ureteral stent 100 is configured to be implanted into and/or placed within a body of a patient such that the ureteral stent 100 extends from a renal pelvis or kidney of the patient to one of a bladder and a ureter of the patient. The ureteral stent 100 is configured to facilitate or help facilitate the movement of fluid within a urinary tract of the patient. The ureteral stent 100 includes an elongate member 110 having a first portion 120 and a second portion 130.

The first portion 120 of the elongate member 110 includes a proximal end portion 124 and a distal end portion 122. The distal end portion 122 of the first portion 120 includes a distal retention structure 128 configured to be disposed within the kidney of the patient. The distal retention structure 128 is configured to help prevent migration of the ureteral stent 100 downwardly toward the bladder and to, thereby, help retain at least a portion of the ureteral stent 100 within the kidney of the patient. In some embodiments, for example, the distal retention structure 128 of the first portion 120 has a shape, such as a loop shape, a "J" shape, a coiled shape, a pig-tail coil shape, a helical coil shape and/or any other shape that is configured to retain at least a portion of the ureteral stent 100 within the kidney of the patient. In some embodiments, the distal end portion 122 of the first portion 120 does not include a distal retention structure 128. In one embodiment, the first portion of the elongate member 110 is substantially rigid. In another embodiment, only a portion (i.e., the distal end portion 122) is sufficiently rigid to retain within the kidney of the patient.

The first portion 120 of the elongate member 110 defines a lumen (not shown in FIG. 1) having an opening (not shown in FIG. 1) at the distal end portion 122 of the first portion 120. Thus, when the stent 100 is placed within a body of a patent such that the first portion 120 is disposed within a kidney of the patient, the first portion 120 of the elongate member 110 is in fluid communication with the kidney. Said another way, the opening of the lumen can receive fluid from the kidney. In some embodiments, however, the opening of the lumen can be at any location along the first portion 120 of the elongate member 110. For example, the opening of the lumen can be located between the proximal end portion 124 and the distal end portion 122. In other embodiments, the lumen can have multiple openings along the first portion 120 of the elongate member 110.

The second portion 130 of the elongate member 110 is configured to be disposed within at least one of the bladder of the patient and the ureter of the patient. The second portion 130 of the elongate member 110 includes a distal end portion 132 and a proximal end portion 134. The distal end portion 132 of the second portion 130 is coupled to or extends from the proximal end portion 124 of the first portion 120 such that the second portion 130 of the elongate member 110 is in fluid communication with the lumen defined by the first portion 120.

The second portion 130 and the first portion 120 of the elongate member 110 can be coupled by any suitable means. For example, the coupling can be a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling). In some embodiments, however, the second portion 130 and the first portion 120 of the elongate member 110 can be monolithically formed.

In some embodiments, the opening of the lumen defined by the first portion 120 of the elongate member 110 can house a portion of the second portion 130 of the elongate member 110. More specifically, in some such embodiments, a portion of the distal end portion 132 of the second portion 130 fits securely within an opening of the lumen defined by the first portion 120 such that the first portion 120 and the second portion 130 are coupled together. Said another way, the distal end portion 132 of the second portion 130 and the opening of the lumen defined by the first portion 120 collectively form an interference fit. In some embodiments, the second portion 130 has a sidewall that defines a lumen (not shown) having an opening (not shown) that can house a portion of the proximal end portion 124 of the first portion 120 such that the first portion 120 and the second portion 130 are coupled together. In other embodiments, however, the opening of the lumen defined by the first portion 120 and the distal end portion 132 of the second portion 130 and/or the opening of the lumen defined by the sidewall of the second portion 130 and the proximal end portion 124 of the first portion 120 can be coupled together via an adhesive, a chemical bond, and/or the like.

In some embodiments, the proximal end portion 134 of the second portion 130 of the elongate member 110 includes a proximal retention structure (not shown) configured to help prevent the migration of the ureteral stent 100 upwardly toward the kidney of the patient and to, thereby, help retain at least a portion of the ureteral stent 100 within the bladder or the ureter of the patient. In some such embodiments, for example, the proximal retention structure of the second portion 130 can have a shape, such as a loop shape, a "J" shape, a coiled shape, a pig-tail coil shape, a helical coil shape and/or any other shape that is configured to retain at least a portion of the ureteral stent 100 within the bladder or the ureter of the patient. In some embodiments, the proximal end portion 134 of the second portion 130 is coupled to a proximal retention structure.

In some embodiments, the proximal end portion 134 of the second portion 130 is shaped to facilitate the removal of the ureteral stent 100 from the body. For example, the proximal end portion 134 of the second portion 130 can include a loop shape to facilitate the grasping of the stent for removal.

The second portion 130 of the elongate member 110 is configured to deliver fluid from a first location of the second portion 130 to a second location of the second portion 130 via capillary action (i.e., capillarity). For example, the second portion 130 can deliver fluid from the distal end portion 132 of the second portion 130 to the proximal end portion 134 of the second portion 130. In this manner, the ureteral stent 100 can move fluid from the kidney to the bladder of the patient. In one embodiment, the second portion 130 of the elongate member 110 is substantially flexible. Specifically, in one embodiment, the second portion 130 of the elongate member 110 is more flexible than the first portion of the elongate member 110.

In some embodiments, the second portion 130 is constructed of a material having "wicking properties" to facilitate capillary action. Such materials attract fluid from locations where fluid is abundant (e.g., the kidney or the distal end portion 132 of the second portion 130) and transport the fluid to a location where fluid is less abundant (e.g., the bladder or the proximal end portion 134 of the second portion 130). In use, the material of the second portion 130 of the elongate member 110 attracts fluid, such as, urine, that accumulates in the kidney such that the fluid is drawn into the small pores of the material. As the material of the second portion 130 becomes more saturated with the fluid, the fluid is transported to the bladder of the patient such that the fluid of the kidney is emptied into the bladder. In some embodiments, the material of the second portion 130 can be, for example, a wicking material. In some embodiments, the material of the second portion 130 can be constructed of a yarn, such as, for example, a multi-stranded yarn having such wicking properties. In some such embodiments, the wicking material can have radio-opacity properties and be constructed of a biocompatible plastic, such as, polypropylene, polyester and/or the like. For example, the material of the second portion 130 can be constructed of a melt spun polypropylene with a high loading of barium sulphate, such as, for example, Micropake (manufactured by Specialty Fibres and Materials Ltd.). In some embodiments, the second portion 130 has a sidewall such that the sidewall is constructed of such material having "wicking properties" to facilitate capillary action, as described above.

The second portion 130 of the elongate member 110 can have any size and/or shape to facilitate the moving of fluid from a first location to a second location via capillary action. In some embodiments, the second portion 130 of the elongate member 110 has a sidewall that defines a lumen (not shown in FIG. 1) such that fluid from the kidney can be transported to the bladder of the patient via the lumen defined by the sidewall of the second portion 130 and/or via capillary action through the sidewall.

In some embodiments, the second portion 130 has a substantially tubular shape with a circular cross-section. In other embodiments, the second portion 130 of the elongate member 110 has an oval cross-section, a star cross-section and/or any other shaped cross-section to facilitate the removal of fluids from the kidney of the patient.

In some embodiments, the second portion 130 of the elongate member 110 is substantially solid (i.e., devoid of a lumen). In such embodiments, the fluid is transported from a first location of the second portion 130 to a second location of the second portion 130 solely via capillary action.

Figure 2:
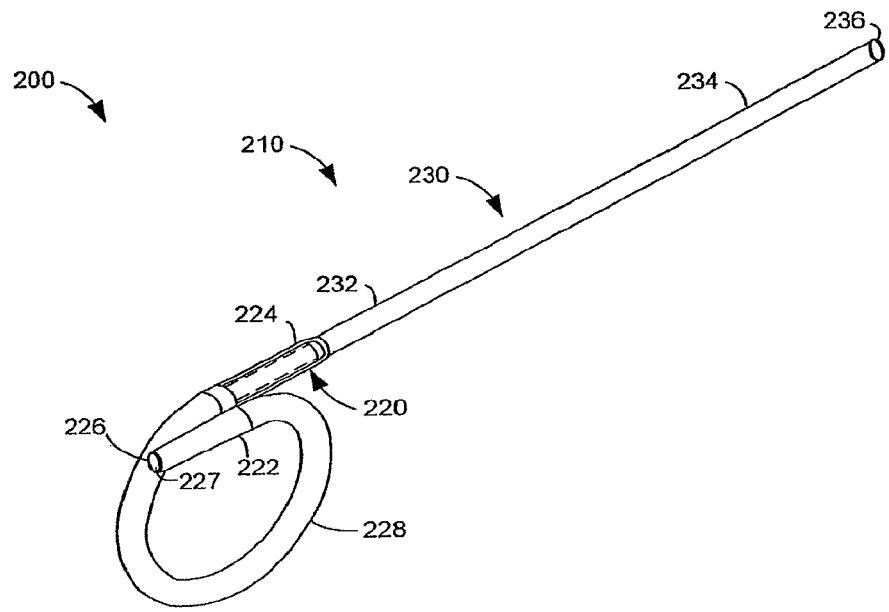
FIG. 2 is a perspective view of a ureteral stent according to an embodiment.

FIG. 2 is a perspective view of a ureteral stent 200 according to an embodiment. The ureteral stent 200 is configured to be implanted into and/or placed within a body of a patient such that the ureteral stent 200 extends from a kidney of the patient to one of a bladder and a ureter of the patient. The ureteral stent 200 is configured to facilitate or help facilitate the movement of fluid within a urinary tract of the patient. The ureteral stent 200 includes an elongate member 210 having a first portion 220 and a second portion 230.

The first portion 220 of the elongate member 210 includes a distal end portion 222 and a proximal end portion 224. The distal end portion 222 of the first portion 220 includes a distal retention structure 228 configured to be disposed within the kidney of the patient. The distal retention structure 228 has a pig-tail shape to help prevent migration of the ureteral stent 200 downwardly toward the bladder and to, thereby, help retain at least a portion of the ureteral stent 200 within the kidney of the patient.

In other embodiments, the distal retention structure 228 of the first portion 220 has a "3" shape, a coiled shape, a loop shape, a helical coil shape and/or any other shape to prevent such downwardly migration of the ureteral stent 200. In some embodiments, the distal end portion 222 of the first portion 220 does not include a distal retention structure 228.

The first portion 220 of the elongate member 210 is constructed of a substantially rigid bio-compatible plastic, such as polypropylene, polycarbonate or glass-filled polycarbonate. In other embodiments, the first portion of the elongate member is constructed of bio-compatible materials, such as stainless steel, Nitinol or the like.

The first portion 220 of the elongate member 210 defines a lumen 227 having an opening 226 at the distal end portion 222 of the first portion 220. Thus, when the stent 200 is placed within a body of a patient such that the first portion 220 is disposed within a kidney of the patient, the first portion 220 is in fluid communication with the kidney of the patient. In this manner, fluids, such as, urine, that accumulate within the kidney can be evacuated via the lumen 227 defined by the first portion 220. In some embodiments, however, the opening 226 of the lumen 227 can be at any location along the first portion 220 of the elongate member 210. For example, the opening 226 of the lumen 227 can be located between the proximal end portion 224 and the distal end portion 222. In some embodiments, the lumen 227 can have multiple openings along the first portion 220 of the elongate member 210.

The second portion 230 of the elongate member 210 is configured to be disposed within at least one of the bladder of the patient and the ureter of the patient. The second portion 230 of the elongate member 210 includes a distal end portion 232, a proximal end portion 234, and a sidewall (not shown in FIG. 2) that defines a lumen 236 therethrough. The distal end portion 232 of the second portion 230 is coupled to or extends from the proximal end portion 224 of the first portion 220 such that the second portion 230 of the elongate member 210 is in fluid communication with the lumen 227 defined by the first portion 220. Said another way, the lumen 227 defined by the first portion 220 of the elongate member 210 is in fluid communication with the lumen 236 defined by the sidewall of the second portion 230 of the elongate member 210.

As shown in FIG. 2, the second portion 230 of the elongate member 210 has a substantially tubular shape with an outer diameter that is smaller than an outer diameter of the first portion 220 of the elongate member 210. Additionally, the outer diameter of the second portion 230 is substantially the same as an inner diameter of the first portion 220. Said another way, the diameter of the lumen 227 defined by the first portion 220 is substantially the same as the outer diameter of the second portion 230. As a result, a portion of the distal end portion 232 of the second portion 230 is received by an opening (not shown in FIG. 2) of the lumen 227 defined by the first portion 220 such that the portion of the distal end portion 232 of the second portion 230 fits securely within the opening of the lumen 227. Said another way, the opening of the lumen 227 defined by the first portion 220 and the portion of the distal end portion 232 of the second portion 230 form an interference fit such that the first portion 220 and the second portion 230 are collectively coupled. In some embodiments, the portion of the distal end portion 232 of the second portion 230 and the opening of the lumen 227 defined by the first portion 220 are coupled such that they form a substantially fluid-tight seal. In some embodiments, the opening of the lumen 227 of the first portion 220 and the portion of the distal end portion 232 of the second portion 230 can be coupled together via an adhesive, a chemical bond, and/or the like. In other embodiments, the second portion of the elongate member has an outer diameter that is equal to or larger than the first portion of the elongate member. In some embodiments, an opening (not shown in FIG. 2) of the lumen 236 defined by the sidewall of the second portion 230 can house a portion of the proximal end portion 224 of the first portion 220 such that the first portion 220 and the second portion 230 are coupled together, as described above.

In some embodiments, the second portion 230 can be coupled to the first portion 220 of the elongate member 210 by any suitable means. For example, the coupling can be a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling). In some embodiments, however, the second portion 230 and the first portion 220 can be monolithically formed.

The second portion 230 of the elongate member 210 (i.e., the sidewall of the second portion 230) is constructed of a multi-stranded yarn, such as, for example, Micropake, which is a melt spun polypropylene with a high loading of barium sulphate having radio-opacity properties. Such yarn can be manufactured, for example, by Specialty Fibres and Materials Ltd. The multi-stranded yarn is braided into a tube shape. In some embodiments, the multi-stranded yarn can be woven in a long strip, such as, for example, a tape. In some embodiments, the multi-stranded yarn can be stretched as individual yarns and/or the like. Such yarn has wicking properties such that the yarn is configured to transport fluids from a high abundance area to a low abundance area, as described above. Additionally, the yarn allows for a softer second portion 230 of the elongate member 210, which enhances patient comfort.

When the ureteral stent 200 is disposed within a body of a patient such that the ureteral stent 200 extends from a kidney to a bladder or ureter, fluids, such as, urine, that accumulate within the kidney of the patient are received by the opening 226 of the lumen defined by the first portion 220 of the elongate member 220. The fluids travel then within the lumen defined by the first portion 220. The fluids are received by the lumen 236 defined by the sidewall of the second portion 230 when the fluids reach the proximal end portion 224 of the first portion 220. The fluids move through the lumen 236 from the distal end portion 232 to the proximal end portion 234 of the second portion 230 until the fluids are disposed within the bladder or ureter of the patient.

In some instances, the lumen 236 defined by the sidewall of the second portion 230 of the elongate member 210 can collapse and, as a result, the fluids are blocked from traveling through the lumen 236. In some such instances, the fluids can be transported from the blocked location within the lumen 236 defined by the sidewall of the second portion 230 to the bladder or ureter of the patient via capillary action. Specifically, the fluids can be drawn into the sidewall of the second portion 230 such that the fluids move from the blocked location to the proximal end portion 234 of the second portion 230 via capillary action within the sidewall. Once the fluids reach the proximal end portion 234 of the second portion 230, the fluid is disposed within the bladder or the ureter of the patient. In this manner, the fluids are being transported from a location within the body that has a high abundance of fluids (i.e., the kidney) to a location within the body that has a low abundance of fluids (i.e., the bladder or ureter) without the use of the lumen 236 defined by the sidewall of the second portion 230.

In some embodiments, the proximal end portion 234 of the second portion 234 can include a proximal retention structure to help retain a portion of the second portion 234 within the bladder or the ureter of the patient, as described above.

Figure 3:
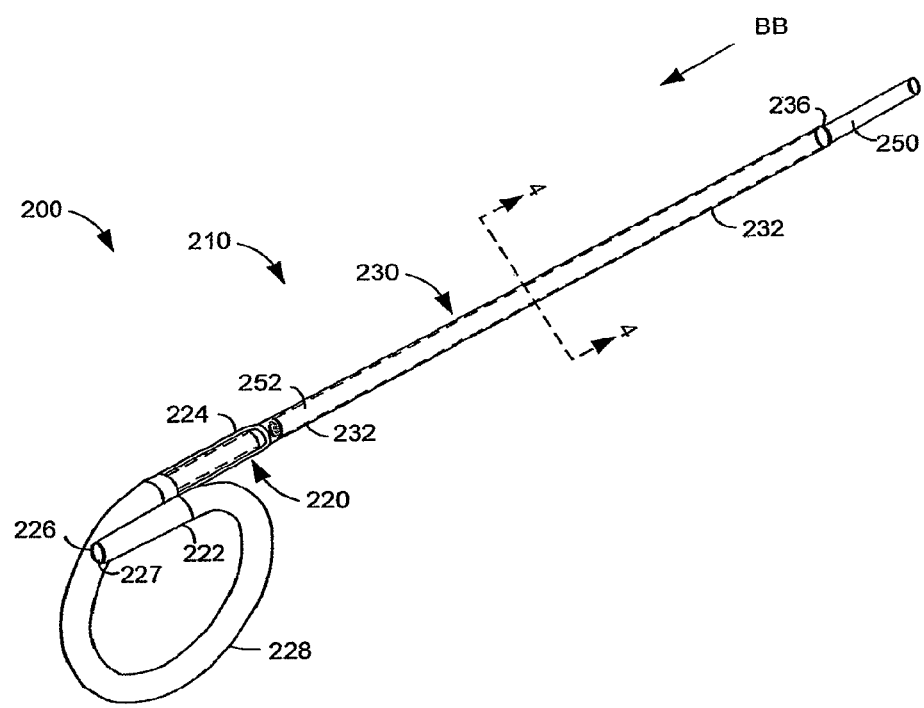
FIG. 3 is a perspective view of the ureteral stent shown in FIG. 2 and a pusher, according to an embodiment.
Figure 5:
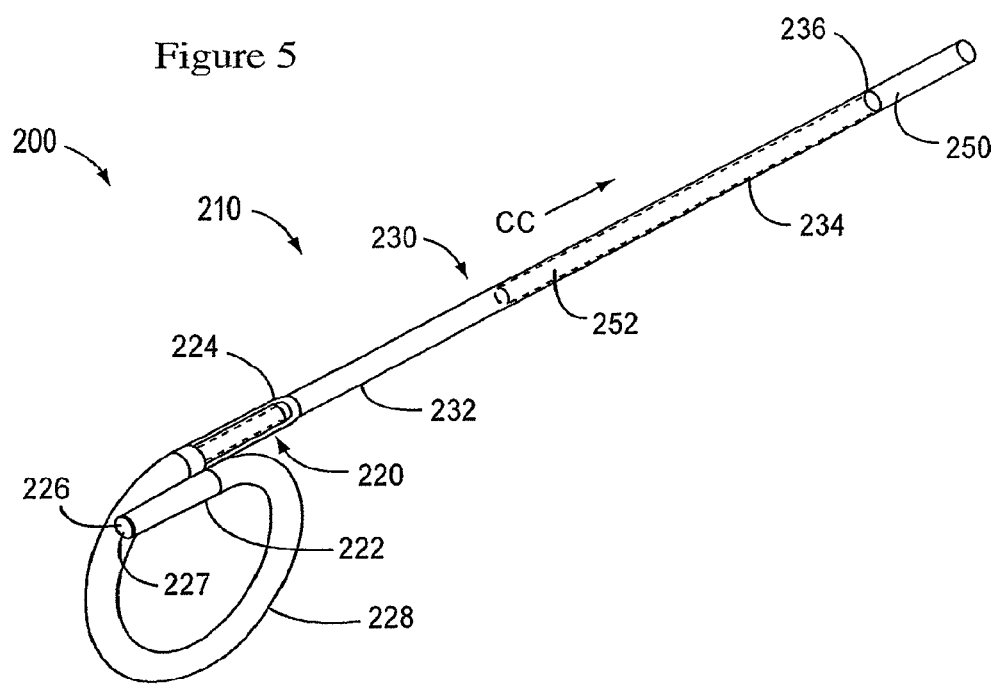
FIG. 5 is a perspective view of the ureteral stent shown in FIG. 2 and a pusher, according to an embodiment.

FIGS. 3 and 5 are a perspective views of the ureteral stent 200 in a first configuration and a second configuration, respectively, according to an embodiment of the invention. The ureteral stent 200 is configured to be inserted into a body of the patient via a pusher 250. The pusher 250, which is substantially rigid, is received by the lumen 236 defined by the sidewall of the second portion 230 such that pusher 250 is substantially housed within the lumen 236 during insertion.

Figure 4:
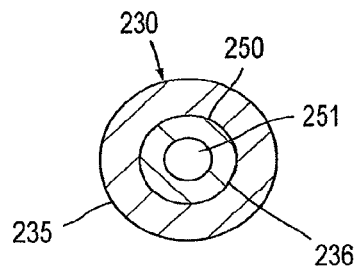
FIG. 4 is a cross-sectional view of the ureteral stent and the pusher shown in FIG. 3 taken along line 4-4.

FIG. 4 is a cross-sectional view of the pusher 250 disposed within the lumen 236 of the second portion 230. In the illustrated embodiment, the pusher 250, which has a substantially circular cross-section, has a diameter substantially the same as the inner diameter of the lumen 236 of the second portion 230. In some embodiments, the pusher 250 has a diameter that is smaller than the inner diameter of the lumen 236.

Although the pusher 250 is described above having a substantially circular cross-sectional shape, in some embodiments, the pusher 250 can have any cross-sectional shape to facilitate the movement of the pusher 250 within the lumen 236 of the second portion 230 and/or to facilitate the movement of the ureteral stent 200 within the body.

Referring to FIG. 3, the pusher 250 is moved in direction BB within the lumen 236 of the second portion 230. A distal end portion 252 of the pusher 250 is configured to engage the proximal end portion 224 of the first portion 220. Thus, any additional movement of the pusher 250 in direction BB results in the ureteral stent 200 being moved in the direction BB. Accordingly, the ureteral stent 200 may be moved within a body of a patient to place the ureteral stent 200. For example, the ureteral stent 200 may be moved via the pusher 250 along a path defined by a guide wire to place the ureteral stent 200 within the body of the patient.

As shown in FIG. 5, the pusher 250 is removed from the lumen 236 of the second portion 230 by moving the pusher in direction CC (for example, after the ureteral stent 200 is positioned within the body of the patient). More specifically, the pusher 250 moves relative to the second portion 230 of the elongate member 210 in direction CC such that the ureteral stent 200 remains in the body. In this manner, the pusher 450 is removed from the body.

Figure 6:
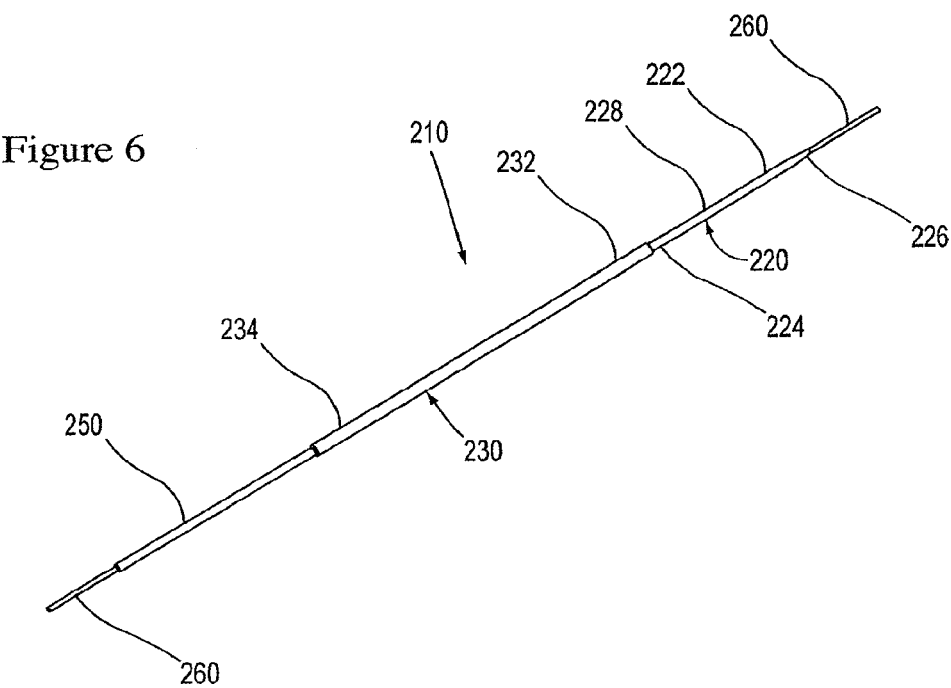
FIG. 6 is a perspective view of the ureteral stent shown in FIG. 2, a pusher and a guide wire, according to an embodiment.
Figure 6A:
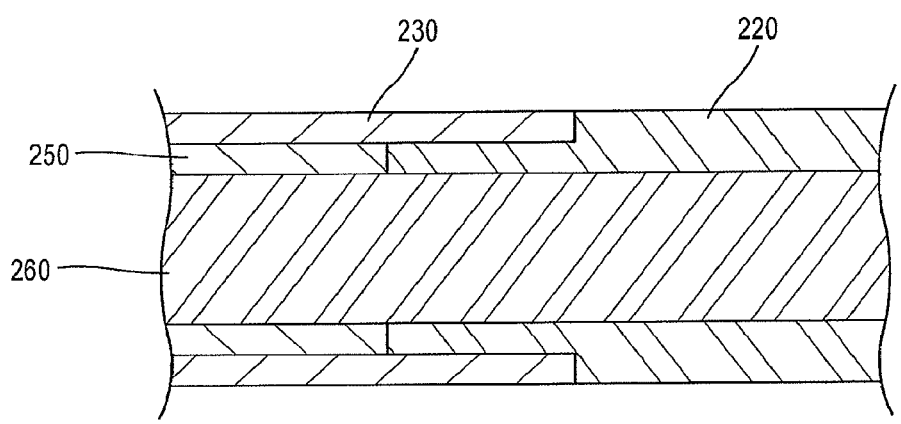
FIG. 6A is a longitudinal cross-sectional view of the ureteral stent shown in FIG. 2, a pusher and a guide wire, according to an embodiment.

In some embodiments, the pusher 250 defines a lumen 251 that is configured to receive a guide wire 260 to facilitate placement of the ureteral stent 200 within a body of a patient. In some such embodiments, the diameter of the lumen 251 defined by the pusher 250 is larger than an outer diameter of the guide wire 260 such that the guide wire 260 can move within the lumen 251. For example, as shown in FIGS. 6 and 6A, the guide wire 260 can be inserted through the lumen defined by the pusher 250, which extends through the lumen 236 defined by the second portion 230 of the stent 200. Additionally, the guide wire 260, which can be constructed of a rigid material, can extend through the lumen 227 defined by the first portion 220 of the stent 200 such that the first portion 220 is placed in a straightened configuration when the guide wire 260 is disposed within the lumen 227. In this manner, the outer diameter of the guide wire 260 is smaller than a diameter of the lumen 227 defined by the first portion 220.

In some embodiments, the guide wire 260 can be configured to facilitate the positioning of the stent 200 within the body. For example, the pusher 250 can be configured to move the stent 200 along the guide wire 260, which can be disposed within the body. Once the stent 200 is positioned within the body, the guide wire 260 can be removed from the body such that the guide wire 260 is removed from the lumen defined by the pusher 250. In this manner, the guide wire 260 is removed from the lumen 227 defined by the first portion 220 of the stent 200 such that the original curled configuration of the first portion 220 is resumed.

In some embodiments, the ureteral stent 200 and the pusher 250 can be pre-packaged together such that the pusher 250 is disposed within the lumen 236 of the second portion 230 and engaged with the proximal end portion 224 of the first portion 220. In this manner, any movement of the pusher 250 in direction BB results in the ureteral stent 200 being moved in direction BB.

Figure 7:
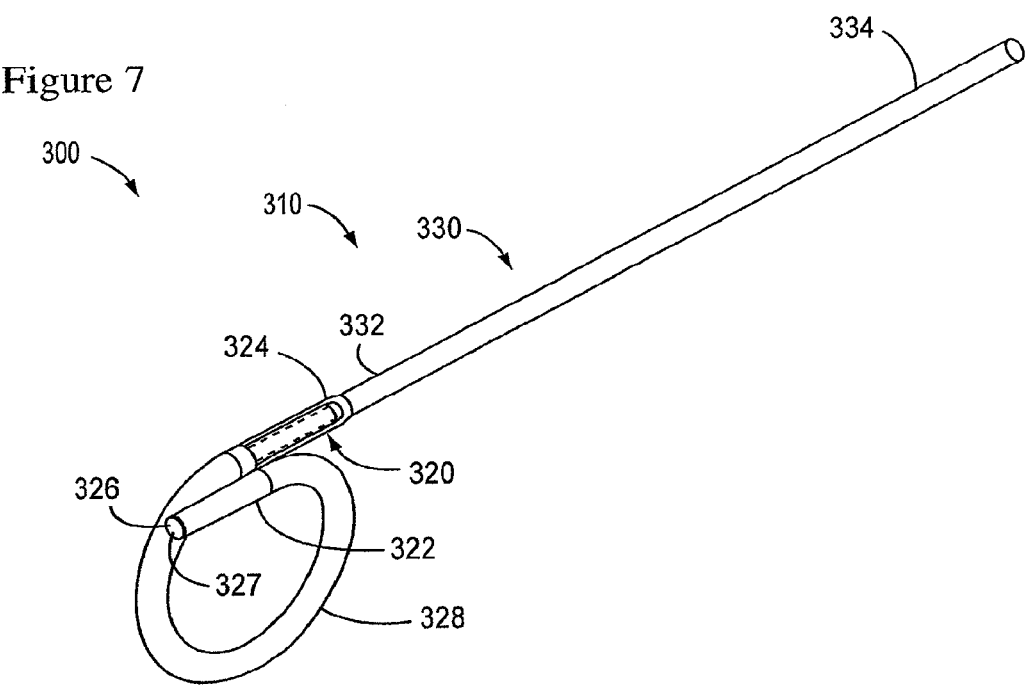
FIG. 7 is a perspective view of a ureteral stent according to an embodiment.

FIG. 7 is a perspective view of a ureteral stent 300 according to an embodiment. The ureteral stent 300 is configured to be implanted into and/or placed within a body of a patient such that the ureteral stent 300 extends from a kidney of the patient to one of a bladder and the ureter of the patient. The ureteral stent 300 is configured to facilitate or help facilitate the movement of fluid within a urinary tract of the patient. The ureteral stent 300 includes an elongate member 310 having a first portion 320 and a second portion 330.

The first portion 320 of the elongate member 310 includes a distal end portion 322 and a proximal end portion 324. The distal end portion 322 of the first portion 320 includes a distal retention structure 328 configured to be disposed within the kidney of the patient. The distal retention structure 328 has a pig-tail shape to help prevent migration of the ureteral stent 300 downwardly toward the bladder and to, thereby, help retain at least a portion of the ureteral stent 300 within the kidney of the patient. In some embodiments, the distal retention structure 328 of the first portion 320 can have any shape to prevent such downwardly migration of the ureteral stent 300, as described above. In some embodiments, the distal end portion 322 of the first portion 320 does not include a distal retention structure 328.

The first portion 320 of the elongate member 310 is constructed of a substantially rigid bio-compatible plastic, as described above. In other embodiments, the first portion 320 of the elongate member 310 is constructed of bio-compatible materials, as described above.

The first portion 320 of the elongate member 310 defines a lumen 327 having an opening 326 at the distal end portion 322 of the first portion 320. Thus, when the stent 300 is placed within a body of a patient such that the first portion 320 is disposed within a kidney of a patient, the first portion 320 is in fluid communication with the kidney of the patient. In this manner, fluids, such as, urine, that accumulate within the kidney can be evacuated via the lumen 327 defined by the first portion 320. In some embodiments, the opening 326 of the lumen 327 can be at any location along the first portion 320 of the elongate member 310, as described above. In some embodiments, the lumen 327 can have multiple openings along the first portion 320 of the elongate member 310.

The second portion 330 of the elongate member 310 is configured to be disposed within at least one of the bladder of the patient and the ureter of the patient. The second portion 330 of the elongate member 310 is constructed of a multi-stranded yarn, as described above. The second portion 330 of the elongate member 310 includes the distal end portion 332 and a proximal end portion 334. The distal end portion 332 of the second portion 330 is coupled to the proximal end portion 324 of the first portion 320 such that the second portion 330 of the elongate member 310 is in fluid communication with the lumen defined by the first portion 320. The second portion 330 and the first portion 320 of the elongate member 310 can be coupled by any suitable means, as described above. In some embodiments, the proximal end portion 334 of the second portion 334 can include a proximal retention structure (not shown), as described above.

As shown in FIG. 7, the second portion 330 of the elongate member 310 has a substantially solid tubular shape with an outer diameter that is smaller than an outer diameter of the first portion 320 of the elongate member 310. Additionally, the outer diameter of the second portion 330 is substantially the same as an inner diameter of the first portion 320. Said another way, the diameter of the lumen 327 defined by the first portion 320 is substantially the same as the outer diameter of the second portion 330. As a result, a portion of the distal end portion 332 of the second portion 330 is received by an opening (not shown in FIG. 7) of the lumen 327 defined by the first portion 320 such that the portion of the distal end portion 332 of the second portion 330 fits securely within the opening of the lumen 327, as described above. In some embodiments, the portion of the distal end portion 332 of the second portion 330 and the opening of the lumen 327 defined by the first portion 320 are coupled such that they form a substantially fluid-tight seal. In some embodiments, the opening of the lumen 327 of the first portion 320 and the portion of the distal end portion 332 of the second portion 330 can be coupled together via an adhesive, a chemical bond, and/or the like. In other embodiments, the second portion 330 of the elongate member 310 has an outer diameter that is equal to or larger than the first portion 320 of the elongate member 310. In other such embodiments, the distal end portion 332 of the second portion 330 and the proximal end portion 324 of the first portion 320 can be coupled together via an adhesive, a chemical bond, and/or the like, as described above.

When the ureteral stent 300 is disposed within a body of a patient such that the ureteral stent 300 extends from a kidney to a bladder or ureter, fluids, such as, urine, that accumulate within the kidney of the patient are received by the opening 326 of the lumen defined by the first portion 320 of the elongate member 320. The fluids travel then within the lumen defined by the first portion 320. When the fluids reach the proximal end portion 324 of the first portion 320, the fluids are received by the second portion 330 of the elongate member 310, which is devoid of a central lumen, and delivered to the bladder or ureter of the patient via capillary action. Specifically, the fluids are drawn into the second portion 330 such that the fluids move within small pores of the sidewall from the distal end portion 332 to the proximal end portion 334 of the second portion 330 via capillary action. Once the fluids reach the proximal end portion 334 of the second portion 330, the fluid is disposed within the bladder or ureter of the patient. In this manner, the fluids are being transported from a location within the body that has a high abundance of fluids (i.e., the kidney) to a location within the body that has a low abundance of fluids (i.e., the bladder or ureter) without the use of a central lumen.

Figure 8:
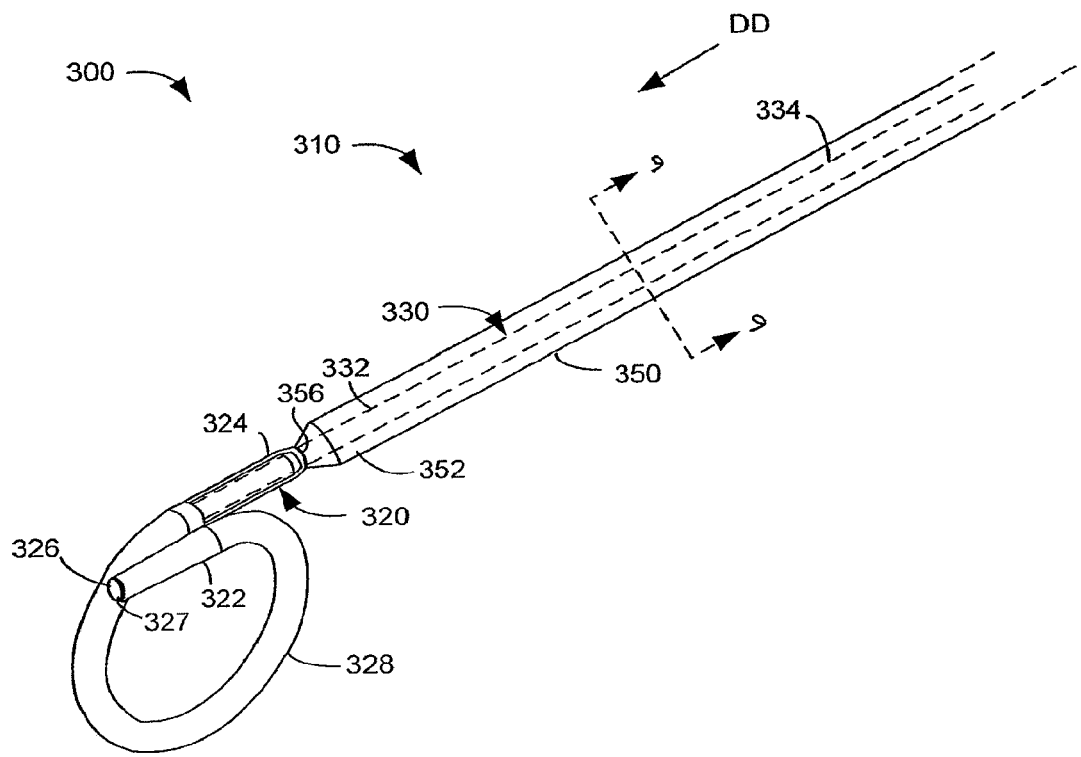
FIG. 8 is a perspective view of the ureteral stent shown in FIG. 7 and a pusher, according to an embodiment.
Figure 10:
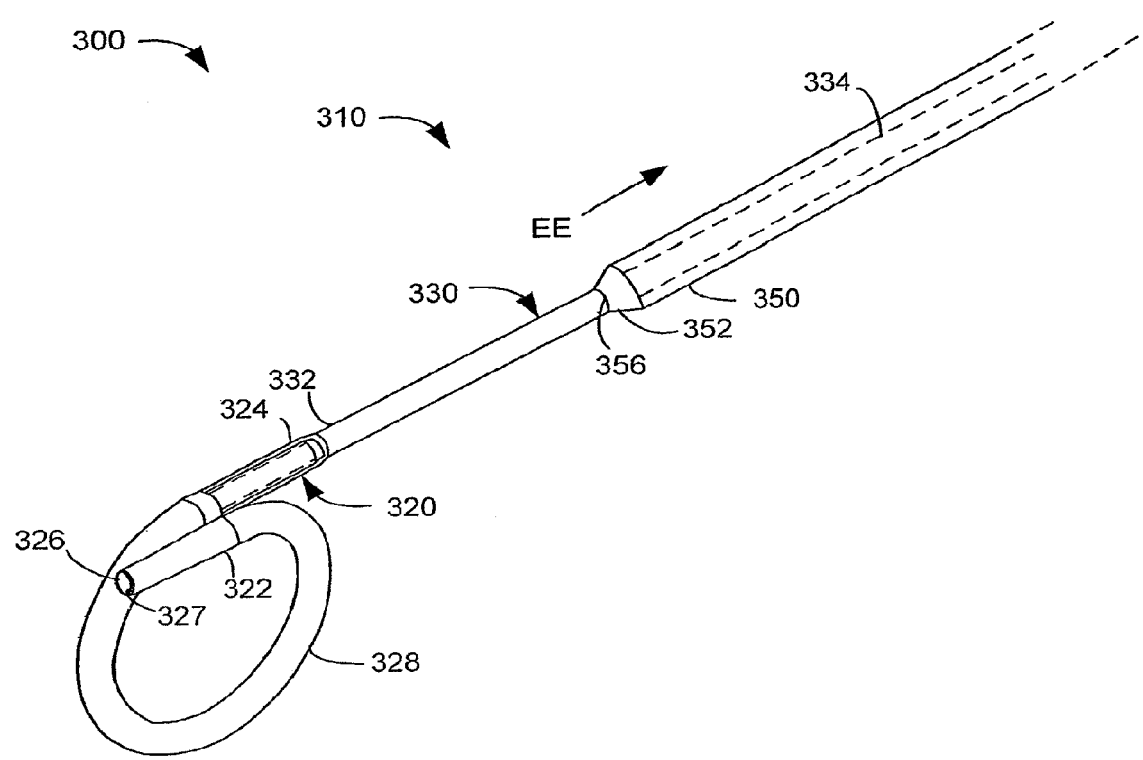
FIG. 10 is a perspective view of the ureteral stent shown in FIG. 7 and a pusher, according to an embodiment.

FIGS. 8 and 10 are a perspective views of the ureteral stent 300 in a first configuration and a second configuration, respectively, according to an embodiment of the invention. The ureteral stent 300 is configured to be inserted into the body of the patient via a pusher 350. The pusher 350, which is substantially rigid, includes a distal end portion 352 and defines a lumen 356 therethrough. The lumen 356 defined by the pusher 350 houses a portion of the second portion 330 of the elongate member 310. In this manner, the pusher 350 can slide along the second portion 330 of the elongate member 310.

Figure 9:
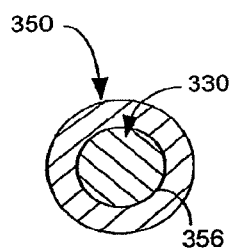
FIG. 9 a cross-sectional view of the ureteral stent and the pusher shown in FIG. 8 taken along line 9-9.

FIG. 9 is a cross-sectional view of the second portion 330 of the elongate member 310 disposed within the lumen 356 defined by the pusher 350. In the illustrated embodiment, the pusher 350 has a substantially circular cross-section. The lumen 356 defined by the pusher 350 has a diameter substantially the same as the diameter of the second portion 330 of the elongate member 310. Said another way, the second portion 330 of the elongate member 310 is in contact with a sidewall of the lumen 356 defined by the pusher 350. In some embodiments, the lumen 356 of the pusher 350 has a diameter that is larger than the outer diameter of the second portion 330. In some embodiments, the second portion 330 of the elongate member 310 defines a lumen (i.e., a guide wire channel) that is configured to receive a guide wire to facilitate placement of the ureteral stent 300 within a body of a patient.

Although the pusher 350 is described above having a substantially circular cross-sectional shape, in some embodiments, the pusher 350 can have any cross-sectional shape to facilitate the movement of the second portion 330 within the lumen 356 defined by the pusher 350 and/or to facilitate the movement of the ureteral stent 300 within the body.

Referring to FIG. 8, the second portion 330 of the elongate member 310 is disposed within the lumen 356 defined by the pusher 350 such that the pusher 350 is moved in direction DD along the second portion 330 of the elongate member 310. The distal end portion 352 of the pusher 350 is configured to engage the proximal end portion 324 of the first portion 320. Thus, any additional movement of the pusher 350 in direction DD results in the ureteral stent 300 being moved in the direction DD. Accordingly, the ureteral stent 300 may be moved within the body of a patient to place the ureteral stent 300. For example, the ureteral stent 300 may be moved via the pusher 350 along a path defined by a guide wire to place the ureteral stent 300 within the body of the patient.

As shown in FIG. 10, the second portion 330 of the elongate member 310 is removed from the lumen 356 defined by the pusher 350 by moving the pusher 350 in direction EE (for example, after the ureteral stent 300 is positioned within the body of the patient). More specifically, the pusher 350 moves relative to the second portion 330 of the elongate member 310 in direction EE such that the ureteral stent 300 remains in the body. In this manner, the pusher 350 is removed from the body.

Although the second portion 330 of the elongate member 310 is illustrated and described as being substantially solid, in some embodiments, the second portion 330 can define a lumen.

In some embodiments, the ureteral stent 300 and the pusher 350 can be pre-packaged together such that second portion 330 is disposed within the lumen 356 defined by the pusher 350 and the pusher 350 engaged with the proximal end portion 324 of the first portion 320. In this manner, any movement of the pusher 350 in direction DD results in the ureteral stent 300 being moved in direction DD.

Figure 11:
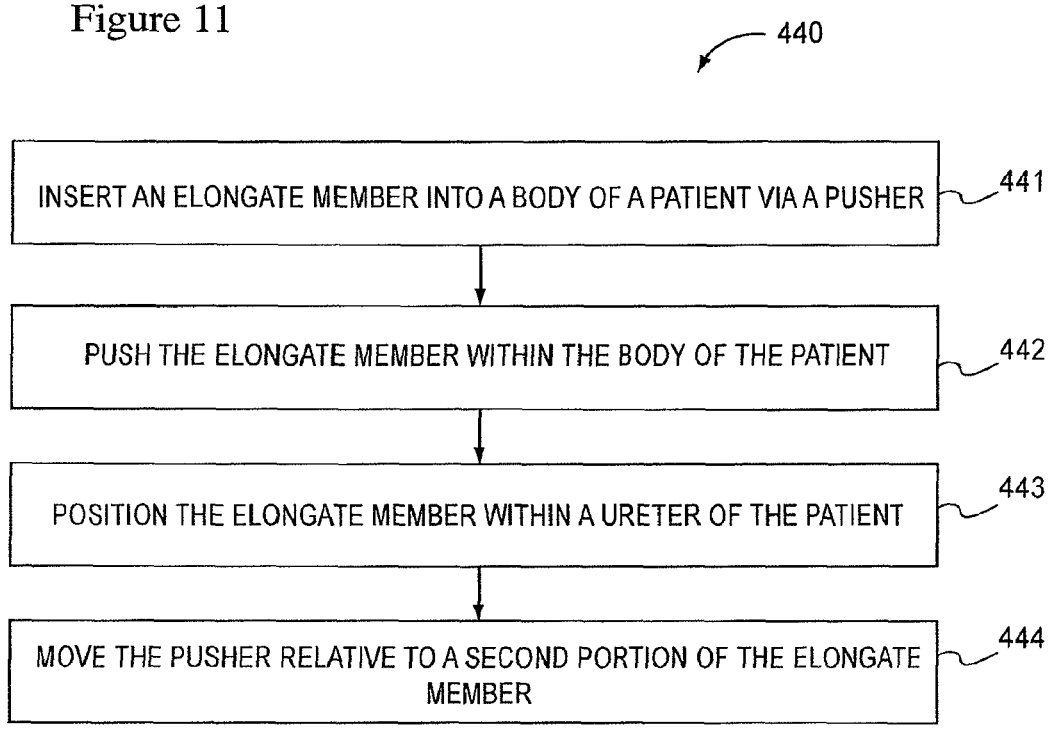
FIG. 11 is a flow chart of a method according to an embodiment.

FIG. 11 is a flow chart of a method 440 of inserting a ureteral stent within a body of a patient according to an embodiment of the invention. The method includes inserting an elongate member into a body of a patient via a pusher, 441. The elongate member includes a first portion and a second portion. The first portion of the elongate member is coupled to the second portion of the elongate member. In some embodiments, the pusher defines a lumen such that a portion of the second portion of the elongate member is housed within the lumen, as described above with reference to FIG. 8. In some embodiments, the second portion defines a lumen such that at least a portion of the pusher is housed within the lumen, as described above with reference to FIG. 3.

The elongate member is pushed within the body of the patient, 442. Specifically, the elongate member is pushed within the body of the patient such that a proximal end portion of the first portion of the elongate member is engaged with a distal end portion of the pusher. In this manner, the pusher pushes against the rigid proximal end portion of the first portion to move the ureteral stent within the body.

The elongate member is positioned within a ureter of the patient, 443. Specifically, the elongate member is positioned within the ureter of the patient such that a distal retention structure coupled to the first portion of the elongate member is disposed within a kidney of the patient and the second portion of the elongate member is disposed within at least one of the bladder and the ureter of the patient. In some embodiments, the positioning includes positioning a proximal retention structure coupled to the second portion of the elongate member such that the proximal retention structure is disposed within the bladder of the patient.

The pusher is moved relative to the second portion of the elongate member, 444. Specifically, the pusher is moved relative to the second portion of the elongate member such that the distal end portion of the pusher is disengaged from the proximal end portion of the first portion of the elongate member. In this manner, the pusher is removed from the body. In some embodiments, the pusher defines a lumen such that the pusher is moved relative to the second portion of the elongate member to remove the portion of the second portion from within the lumen, as described above with reference to FIG. 10. In some embodiments, the second portion of the elongate member defines a lumen such that the pusher is moved relative to the second portion of the elongate member to remove at least a portion of the pusher from within the lumen, as described above with reference to FIG. 5.

In some embodiments, the method can include sliding the ureteral stent along a guide wire within the body. In some such embodiments, the guide wire can be engaged with the first portion of the elongate portion such that the pusher moves the ureteral stent along the guide wire during insertion.

In some embodiments, the method can include inserting the guide wire within a lumen defined by the first portion of the elongate member such that the first portion moves from a first configuration to a second configuration different from the first configuration, when the guide wire is disposed within the lumen. In some such embodiments, the method can include, after the inserting the guide wire, removing the guide wire from the lumen defined by the first portion of the elongate member such that the first portion moves from the second configuration to the first configuration. In some embodiments, for example, the second configuration can be a straightened configuration.

Figure 12:
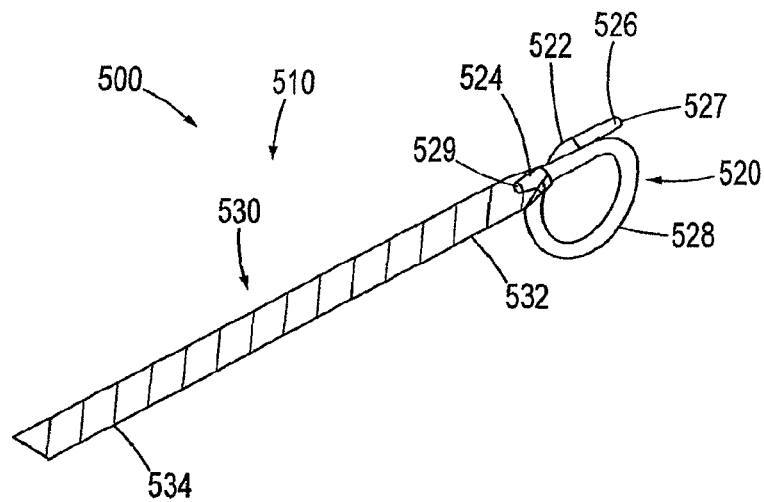
FIG. 12 is a perspective view of a ureteral stent according to an embodiment.

FIG. 12 is a perspective view of a ureteral stent 500 in a first configuration according to an embodiment. The ureteral stent 500 is configured to be implanted into and/or placed within a body of a patient such that the ureteral stent 500 extends from a kidney of the patient to one of a bladder and the ureter of the patient. The ureteral stent 500 is configured to facilitate or help facilitate the movement of fluid within a urinary tract of the patient. The ureteral stent 300 includes an elongate member 510 having a first portion 520 and a second portion 530.

The first portion 520 of the elongate member 510 includes a distal end portion 522 and a proximal end portion 524. The distal end portion 522 of the first portion 520 includes a distal retention structure 528 configured to be disposed within the kidney of the patient. The distal retention structure 528 is configured to move between a first configuration and a second configuration. In the first configuration, as shown in FIG. 12, the distal retention structure 528 has a pig-tail shape to help prevent migration of the ureteral stent 500 downwardly toward the bladder and to, thereby, help retain at least a portion of the ureteral stent 500 within the kidney of the patient. In some embodiments, the distal retention structure 528 of the first portion 520 can have any shape to prevent such downwardly migration of the ureteral stent 500, as described above. In some embodiments, the distal end portion 522 of the first portion 520 does not include a distal retention structure 528.

The first portion 520 of the elongate member 510 is constructed of a substantially rigid bio-compatible plastic, as described above. In other embodiments, the first portion 520 of the elongate member 510 is constructed of bio-compatible materials, as described above.

The first portion 520 of the elongate member 510 defines a lumen 527 having an opening 529 at the proximal end portion 524 and an opening 526 at the distal end portion 522 of the first portion 520. Thus, when the stent 500 is placed within a body of a patient such that the first portion 520 is disposed within a kidney of a patient, the first portion 520 is in fluid communication with the kidney and the ureter of the patient. In this manner, fluids, such as, urine, that accumulate within the kidney can be evacuated via the lumen 527 defined by the first portion 520. Specifically, fluids, such as, urine, are received by the opening 526 at the distal end portion 522 of the first portion 520 and emptied into the ureter of the patient via the opening 529 at the proximal end portion 524 of the first portion 520. In some embodiments, the opening 526 of the lumen 527 can be at any location along the first portion 520 of the elongate member 510, as described above. Similarly, the opening 529 of the lumen 527 can be at any location along the first portion 520 of the elongate member 510. In some embodiments, the lumen 527 can have more than two openings along the first portion 520 of the elongate member 510.

The second portion 530 of the elongate member 510 is configured to be disposed within at least one of the bladder of the patient and the ureter of the patient. The second portion 530 of the elongate member 510 is constructed of a multi-stranded yarn woven into a braided tape configuration such that the second portion 530 is substantially flat. The second portion 530 of the elongate member 510 includes the distal end portion 532 and a proximal end portion 534. The distal end portion 532 of the second portion 530 is coupled to the proximal end portion 524 of the first portion 520.

The second portion 530 is coupled to the first portion 520 of the elongate member 510 by any suitable means. For example, the coupling can be a mechanical coupling (e.g., an interference fit, detents, a threaded coupling, or the like), an electronic coupling (e.g., a magnetic coupling), an adhesive, a chemical bond, a hydraulic coupling and/or a pneumatic coupling (e.g., a vacuum coupling). In some embodiments, however, the second portion 530 and the first portion 520 can be monolithically formed.

As shown in FIG. 12, the second portion 530 of the elongate member 510 has a substantially flat rectangular shape. In some embodiments, the elongate sides of the second portion 530 of the elongate member 510 can be tacked together such that the braided tape forms a lumen (not shown). In some embodiments, the second portion 530 of the elongate member 510 can be rolled such that at least a portion of the distal end portion 532 of the braided tape has a substantially solid tubular shape. In some such embodiments, the portion of the distal end portion 532 having the substantially solid tubular shape has a diameter such that the portion of the distal end portion 532 of the second portion 530 is received by the opening 529 of the lumen 527 defined by the first portion 520. In this manner, the portion of the distal end portion 532 of the second portion 530 fits securely within the opening 529 of the lumen 527.

When the ureteral stent 500 is disposed within a body of a patient such that the ureteral stent 500 extends from a kidney to a bladder or ureter, fluids, such as, urine, that accumulate within the kidney of the patient are received by the opening 526 of the lumen defined by the first portion 520 of the elongate member 520. The fluids travel then within the lumen 527 defined by the first portion 520. When the fluids reach the proximal end portion 524 of the first portion 520, the fluids are evacuated from the lumen 527 via the opening 529 such that the fluids are emptied onto the second portion 530 of the elongate member 510 and delivered to the bladder or ureter of the patient via capillary action. Specifically, the fluids are drawn into the second portion 530 such that the fluids move within small pores of the material of the second portion 530 and move from the distal end portion 532 to the proximal end portion 534 via capillary action. Once the fluids reach the proximal end portion 534 of the second portion 530, the fluid is disposed within the bladder or ureter of the patient. In this manner, the fluids are being transported from a location within the body that has a high abundance of fluids (i.e., the kidney) to a location within the body that has a low abundance of fluids (i.e., the bladder or ureter) without the use of a central lumen.

The second portion 530 of the elongate member 510 may be constructed of a multi-stranded yarn, such as, for example, Micropake, which is a melt spun polypropylene with a high loading of barium sulphate having radio-opacity properties. Such yarn can be manufactured, for example, by Specialty Fibres and Materials Ltd. In some embodiments, the multi-stranded yarn can be woven in a long strip, such as, for example, a tape. In some embodiments, the multi-stranded yarn can be stretched as individual yarns and/or the like. Such yarn has wicking properties such that the yarn is configured to transport fluids from a high abundance area to a low abundance area.

Figure 13:
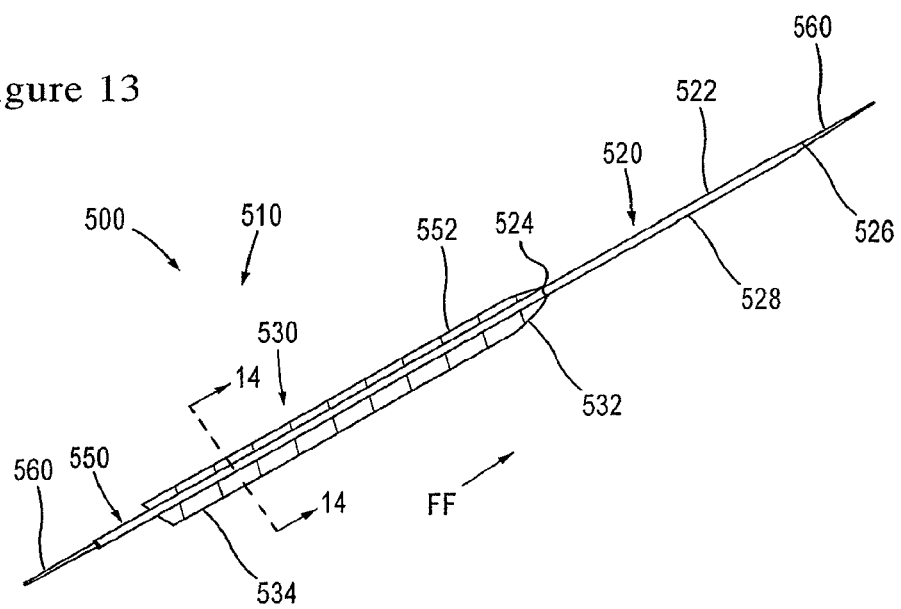
FIG. 13 is a perspective view of the ureteral stent in FIG. 12, a pusher, and a guide wire, according to an embodiment.

FIG. 13 is a perspective view of the ureteral stent 500 in a second configuration, according to an embodiment of the invention. The ureteral stent 500 is configured to be inserted into the body of the patient via a pusher 550 and a guide wire 560. The pusher 550, which is substantially rigid, includes a distal end portion 552 and defines a lumen 556 therethrough. The lumen 556 defined by the pusher 550 is configured to house a portion of the guide wire 560 such that the guide wire 560 can slide within the lumen 556 defined by the pusher 550.

Figure 14:
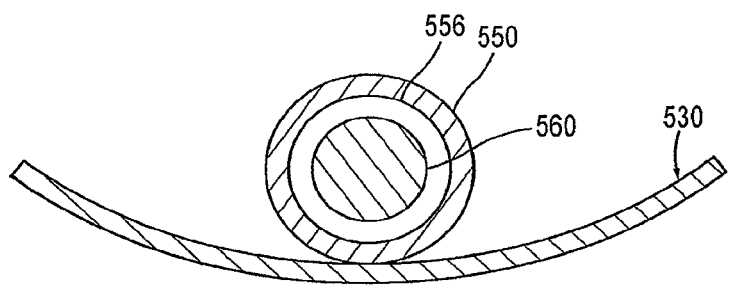
FIG. 14 is a cross-sectional view of the ureteral stent, pusher, and guide wire shown in FIG. 13 taken along line 14-14.

FIG. 14 is a cross-sectional view of the pusher 550 in contact with the substantially flat second portion 530 and the guide wire 560 disposed within the lumen 556 defined by the pusher 550. In the illustrated embodiment, the pusher 550 and the guide wire 560 have substantially circular cross-sections. The lumen 556 defined by the pusher 550 has a diameter substantially larger than a diameter of the guide wire 560. In some embodiments, however, the guide wire 560 has a diameter substantially the same as the diameter of the lumen 556 defined by the pusher 550 such that the guide wire 560 is in contact with a sidewall of the lumen 556 defined by the pusher 550.

Although the pusher 550 and the guide wire 560 are described above having a substantially circular cross-sectional shape, in some embodiments, the pusher 550 and/or the guide wire 560 have other cross-sectional shapes that facilitate the movement of the guide wire 560 within the lumen 556 defined by the pusher 550 and/or to facilitate the movement of the ureteral stent 500 within the body.

Referring to FIG. 13, the guide wire 560, which is substantially rigid, is configured to be housed within the lumen 527 of the first portion 520 of the elongate member 510 such that the guide wire 560 extends from openings 526 and 529. The guide wire 560 is configured to move the distal retention structure 528 of the first portion 520 of the elongate member 510 between the first configuration and the second configuration. Specifically, the guide wire 560 forcibly straightens the distal retention structure 528 such that the distal retention structure 528 is in the second configuration when the guide wire 560 is moved in direction FF within the lumen 527 of the first portion 520. Said another way, the distal retention structure 528 of the first portion 520 of the elongate member 510 is the second configuration (i.e., a straightened configuration) when the guide wire 560 is disposed within the lumen 527 of the first portion 520. As a result, the stent 500 can more easily be inserted and positioned within the patient.

In some embodiments, the lumen 527 defined by the first portion 520 has a diameter substantially larger than a diameter of the guide wire 560. In some embodiments, however, the guide wire 560 has a diameter substantially the same as the diameter of the lumen 527 defined by the first portion 520 such that the guide wire 560 is in contact with a sidewall of the lumen 527 defined by the first portion 520.

While the guide wire 560 is disposed within the lumen 527 defined by the first portion 520, the pusher 550 is threaded onto the guide wire 560 such that a proximal end portion (not shown) of the guide wire 560 is received by the lumen 556 of the pusher 550. In this manner, the pusher 550 can be moved along the guide wire 560 in direction FF until the distal end portion 552 of the pusher 550 engages the proximal end portion 524 of the first portion 520. Thus, any additional movement of the pusher 450 in direction FF results in the ureteral stent 500 being moved in the direction FF along the guide wire 560. Accordingly, the ureteral stent 500 may be moved within the body of a patient to place the ureteral stent 500. Specifically, the ureteral stent 500 may be moved via the pusher 550 along a path defined by the guide wire 560 to place the ureteral stent 500 within the body of the patient.

Although not shown, it is to be understood that the guide wire 560 can be removed from the body and/or the lumen 527 of the first portion 520 of the elongate member 510 by moving the guide wire 560 in a direction opposite to direction FF (for example, after the ureteral stent 500 is positioned within the body of the patient). The distal retention structure 528 of the first portion 520 of the elongate member 510 moves from the second configuration to the first configuration (pig-tail shape shown in FIG. 12) when the guide wire 560 is removed from the lumen 527 of the first portion 520.

Similarly, the pusher 550 can be removed from the body by moving the pusher 550 in a direction opposite to direction FF (for example, after the ureteral stent 500 is positioned within the body of the patient). More specifically, the pusher 550 moves relative to the second portion 530 of the elongate member 510 in a direction opposite to direction FF such that the ureteral stent 500 remains in the body. In this manner, the pusher 550 and/or the guide wire 560 is removed from the body.

In some embodiments, the second portion 530 includes a coupling member (not shown) configured to releaseably couple the pusher 550 and/or the guide wire 560 to the second portion 530. For example, in some embodiments, the second portion 530 includes a loop such that the pusher 550 and/or the guide wire 560 can be passed through the loop. In some embodiments, however, the coupling member of the second portion 530 can releaseably couple the pusher 550 and/or the guide wire 560 to the second portion 530 by any suitable means.

Although the second portion 530 of the elongate member 510 is illustrated and described as being substantially flat and solid, in some embodiments, the second portion 530 can define a lumen.

In some embodiments, the guide wire 560 and the pusher 550 can be pre-packaged together such that guide wire 560 is disposed within the lumen 556 defined by the pusher 350. In some embodiments, the ureteral stent 500, the guide wire 560 and the pusher 350 can be pre-packaged together such that the guide wire 560 is disposed within the lumen 527 defined by the first portion 520 and the lumen 556 defined by the pusher 550. Additionally, in some such embodiments, the distal end portion 552 of the pusher 550 can be engaged with the proximal end portion 524 of the first portion 520. In this manner, any movement of the pusher 550 in direction FF results in the ureteral stent 500 being moved in direction FF along the guide wire 560.

Figure 15:
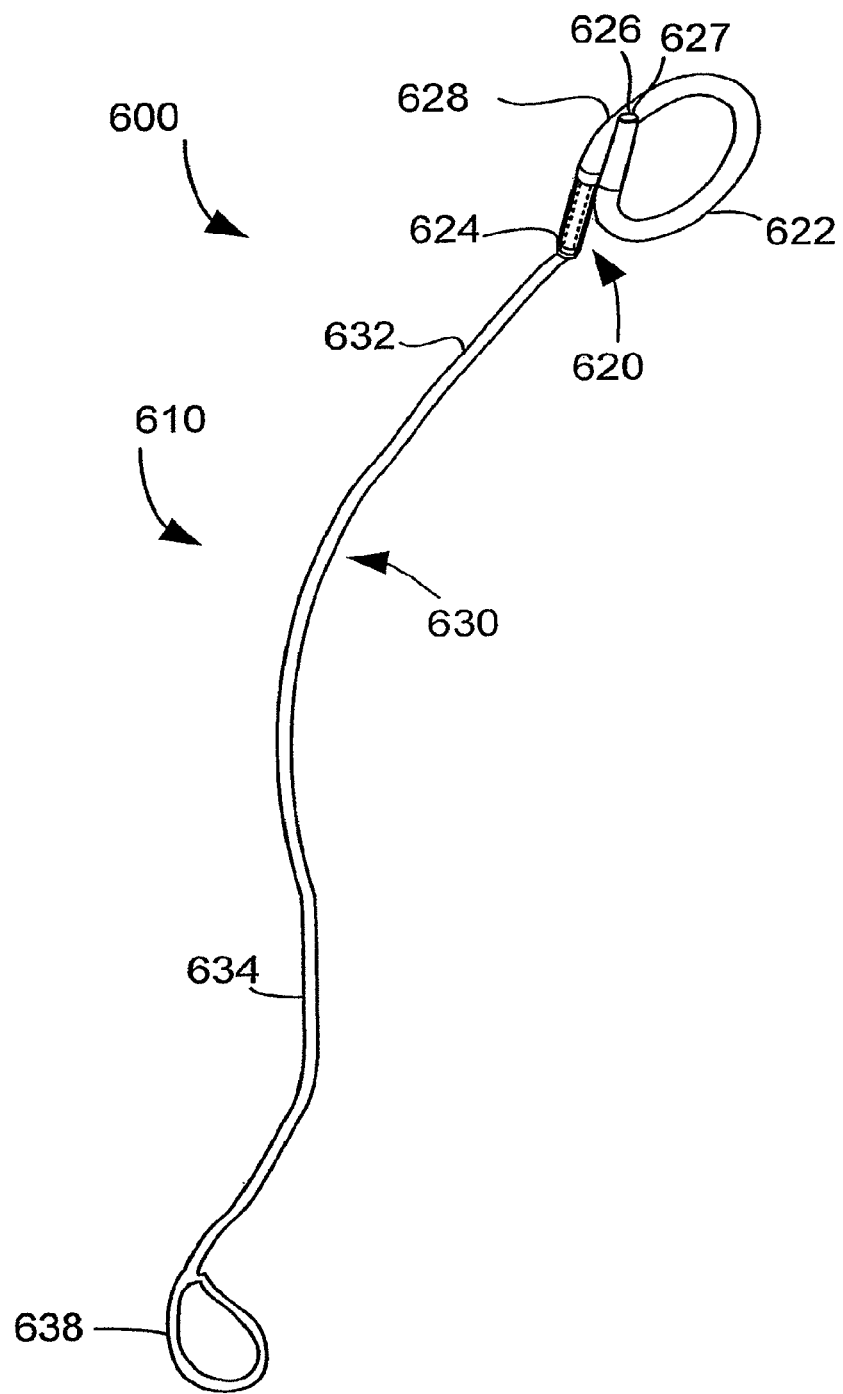
FIG. 15 is a perspective view of a ureteral stent according to an embodiment.

FIG. 15 is a perspective view of a ureteral stent 600 according to an embodiment of the invention. The ureteral stent 600 is configured to be implanted into and/or placed within a body of a patient such that the ureteral stent 600 extends through a kidney of the patient to a bladder of the patient. In this manner, the ureteral stent 600 is configured to facilitate or help facilitate the movement of fluid within a urinary tract of the patient. The ureteral stent 600 includes an elongate member 610 having a first portion 620 and a second portion 630.

The first portion 620 of the elongate member 610 includes a distal end portion 622 and a proximal end portion 624. The distal end portion 622 of the first portion 620 includes a distal retention structure 628 configured to be disposed within the kidney of the patient. The distal retention structure 628 of the first portion 620 has a pig-tail shape to help prevent the ureteral stent 600 from migrating downward toward the bladder and, thereby, to retain the position of the ureteral stent 600 within the body. In some embodiments, the distal retention structure 628 of the first portion 620 can have any shape to prevent such downwardly migration of the ureteral stent 600, as described above. In some embodiments, the distal end portion 622 of the first portion 620 does not include a distal retention structure 628.

The first portion 620 of the elongate member 610 is constructed of a substantially rigid bio-compatible plastic, as described above. In other embodiments, the first portion 620 of the elongate member 610 is constructed of bio-compatible materials, as described above.

The first portion 620 of the elongate member 610 defines a lumen 627 having an opening 626 at the distal end portion 622 of the first portion 620. Thus, when the stent 600 is placed within a body of a patient such that the first portion 620 is disposed within a kidney of the patient, the first portion 620 of the elongate member 610 is in fluid communication with the kidney of the patient. In this manner, fluids, such as, urine, that accumulate within the kidney can be evacuated via the lumen 627 defined by the first portion 620. In some embodiments, the opening 626 can be at any location along the first portion 620 of the elongate member 610, as described above. In some embodiments, the lumen 627 can have multiple openings along the first portion 620 of the elongate member 610.

The second portion 630 of the elongate member 610, which is configured to be disposed within the ureter and the bladder of the patient, has a substantially solid cylindrical shape and is constructed of a multi-stranded yarn having wicking properties, such as, for example, Micropake. The second portion 630 of the elongate member 610 includes the distal end portion 632 and a proximal end portion 634. The distal end portion 632 of the second portion 630 is coupled to the proximal end portion 624 of the first portion 620 such that the second portion 630 is in fluid communication with the lumen defined by the first portion 620. More specifically, an opening of the lumen 627 defined by the first portion 620 receives a portion of the distal end portion 632 of the second portion 630 of the elongate member 610 such that the first portion 620 and the second portion 630 are collectively coupled together, as described above. The outer diameter of the distal end portion 632 of the second portion 630 is substantially the same as the diameter of the lumen 627 defined by the first portion 620 such that a fluid tight seal is formed when the portion of the distal end portion 632 of the second portion 630 is disposed within the opening of the lumen 627 defined by the first portion 630, as described above. In some embodiments, however, the opening of the lumen 627 defined by the first portion 620 and the portion of the distal end portion 632 of the second portion 630 can be coupled via an adhesive, a chemical bond, and/or the like. In some embodiments, the second portion 630 has a sidewall (not shown in FIG. 15) the defines a lumen (not shown in FIG. 15) having an opening (not shown in FIG. 15) that can house a portion of the proximal end portion 624 of the first portion 620 such that the first portion 620 and the second portion 630 are coupled together.

The proximal end portion 634 of the second portion 630 is configured to be disposed in the bladder of the patient. The proximal end portion 634 includes a loop shape 638, which is configured to facilitate the removal of the ureteral stent 600 from the body. Specifically, the loop 638 of the proximal end portion 634 of the second portion 630 facilitates the grasping of the stent 600 for removal. As shown in FIG. 15, the loop 638 and the second portion 630 are a monolithic structure. In some embodiments, the loop 638 can be made of a different material than the second portion 630 such that the loop 638 and the second portion 630 are coupled together. In some embodiments, the proximal end portion 634 of the second portion 630 can include a proximal retention structure (not shown), as described above.

Figure 16:
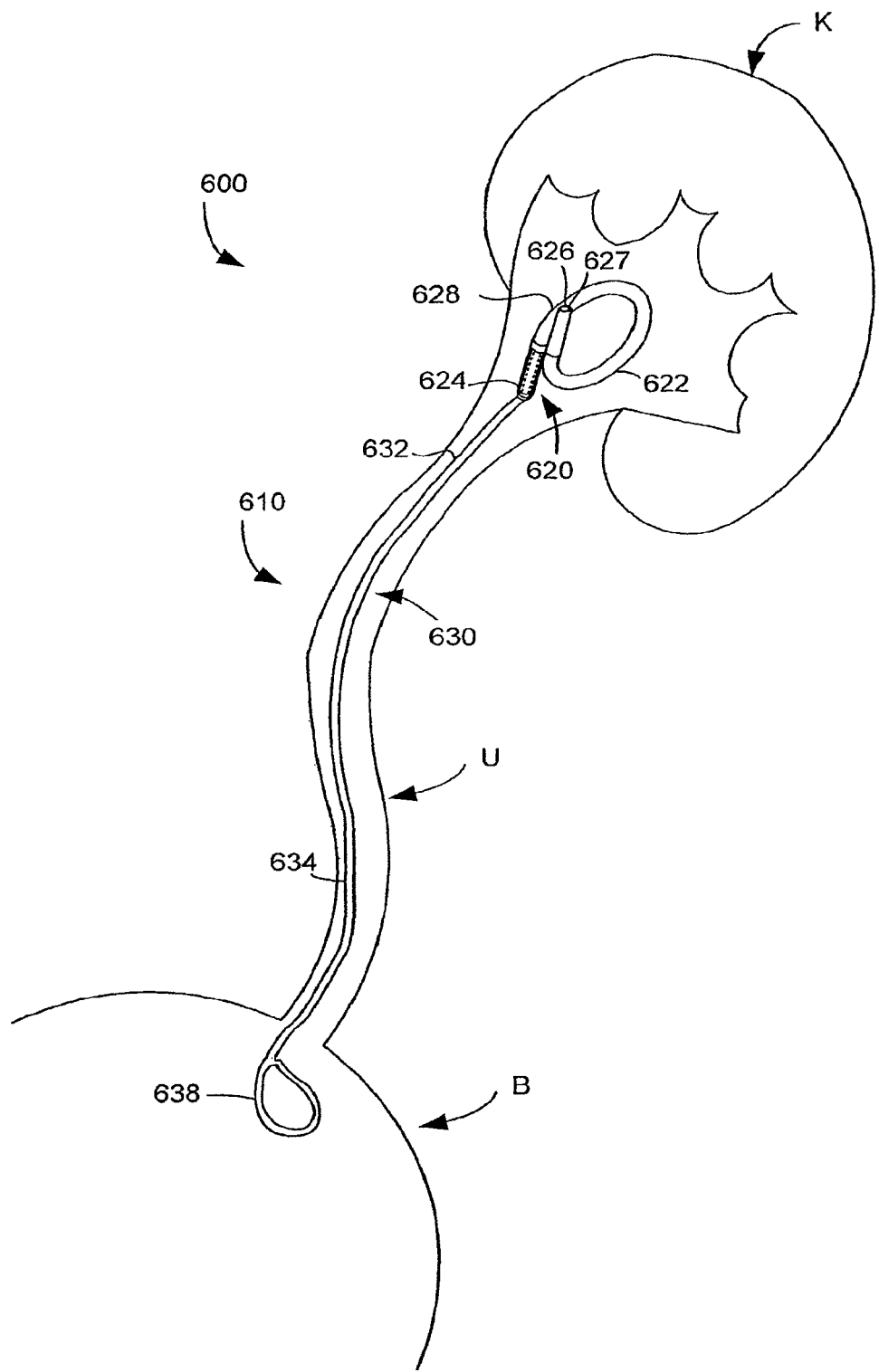
FIG. 16 is a perspective view of the ureteral stent shown in FIG. 15 disposed within a body of a patient.

FIG. 16 is a perspective view of the ureteral stent 600 disposed within a body, according to an embodiment of the invention. The ureteral stent 600 is implanted into and/or placed within a body of a patient such that the ureteral stent 600 extends through a ureter U from a kidney K of the patient to a bladder B of the patient. Specifically, the distal retention structure 628 of the first portion 620 is disposed within the kidney K of the patient. The pig-tail shape of the distal retention structure 628 has a size that is greater than a size of the opening of the ureter U such that the distal retention structure 628 of the first portion 620 prevents the ureteral stent 600 from migrating downward toward the bladder B and, thereby, retains the position of the ureteral stent 600 within the body. Although the first portion 620 of the elongate member 610 is illustrated in FIG. 16 as being disposed within the kidney K of the patient, in some embodiments, a portion of the first portion 620 of the elongate member 610 is disposed within the ureter U of the patient.

The second portion 630 of the elongate member 610 is disposed within the ureter U and the bladder B of the patient. A portion of the proximal end portion 634 of the second portion 630, including the loop shape 638 is disposed in the bladder B of the patient. As discussed above, the loop 638 of the proximal end portion 634 of the second portion 630 facilitates the grasping of the stent 600 for removal.

In use, fluids, such as, urine, accumulate within the kidney K of the patient. Such fluids are received by the opening 626 of the lumen 627 defined by the first portion 620 of the elongate member 620 such that the fluids travel within the lumen 627. When the fluids reach the proximal end portion 624 of the first portion 620, the fluids are received by the second portion 630 of the elongate member 610, which is devoid of a central lumen, and delivered to the bladder B of the patient via capillary action. Specifically, the fluids are drawn into the substantially solid sidewall of the second portion 630 such that the fluids move within small pores of the sidewall from the distal end portion 632 to the proximal end portion 634 of the second portion 630 via capillary action. Once the fluids reach the proximal end portion 634 of the second portion 630, the fluid is disposed within the bladder B of the patient. In this manner, the fluids are being transported from a location within the body that has a high abundance of fluids (i.e., the kidney K) to a location within the body that has a low abundance of fluids (i.e., the bladder B).

Although the second portion 630 of the elongate member 610 is illustrated in FIGS. 15 and 16 as having a solid cylindrical shape, in some embodiments, as described above, the second portion 630 of the elongate member 610 can have a sidewall that defines a lumen.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

In some embodiments, the distal retention structure of the first portion of the elongate member is a separate structure such that the distal retention structure is coupled to the distal end portion of the first portion of the elongate member. In other embodiments, the distal retention structure and the first portion of the elongate member are a monolithic structure.

In some embodiments, the distal retention structure can have a sidewall defining multiple lumens in fluid communication with the kidney to facilitate the evacuation of fluids from the kidney of the patient.

In some embodiments, the ureteral stent can include an opening through which a guide wire can be inserted to facilitate the movement and/or placement of the stent within the body. In some embodiments, the pusher can include an opening through which a guide wire can be inserted to facilitate the movement and/or the placement of the stent within the body.

In some embodiments, a ureteral stent includes an elongate member having a first portion and a second portion. The second portion has a sidewall that defines a lumen. The first portion is coupled to the second portion and is configured to be disposed within a kidney of a patient. The sidewall of the second portion of the elongate member is configured to deliver fluid from a first location of the sidewall of the second portion to a second location of the sidewall of the second portion via capillary action. The second portion of the elongate member is configured to be disposed within at least one of a bladder of a patient and a ureter of the patient.

In some embodiments, the first portion of the elongate member defines a lumen and at least a portion of the second portion of the elongate member is disposed within the lumen.

In some embodiments, the second portion of the elongate member is constructed of a multi-stranded material. In some embodiments the second portion of the elongate member is constructed of a yarn.

In some embodiments, the second portion of the elongate member has a configuration selected from a group consisting of a braided tube configuration, a long woven strip configuration and a stretched configuration.

In some embodiments, the second portion of the elongate member is constructed of a melt spun polypropylene with a high loading of barium sulphate.

In some embodiments, the ureteral stent includes a proximal retention structure configured to be disposed within the bladder of a patient. The proximal retention structure is coupled to the second portion of the elongate member.

In some embodiments, the ureteral stent includes a distal retention structure configured to be disposed within the kidney of the patent. The distal retention structure is coupled to the first portion of the elongate member.

In some embodiments, the first portion is coupled to the second portion via an interference fit.

In some embodiments, at least a portion of the first portion is disposed within the lumen defined by the sidewall of the second portion.

In some embodiments, the second portion of the elongate member is substantially flexible.

In some embodiments, the first portion of the elongate member is substantially rigid.

In some embodiments, the second portion of the elongate member is more flexible than the first portion of the elongate member.

In some embodiments, a ureteral stent includes an elongate member having a first portion and a second portion. The second portion has a sidewall that defines a lumen. The first portion is coupled to the second portion. The first portion is configured to be disposed within a kidney of a patient. The sidewall of the second portion of the elongate member configured to deliver fluid from a first location of the sidewall of the second portion to a second location of the sidewall of the second portion via wicking. The second portion of the elongate member is configured to be disposed within at least one of a bladder of a patient and a ureter of the patient.

In some embodiments, the first portion of the elongate member defines a lumen and at least a portion of the second portion of the elongate member is disposed within the lumen.

In some embodiments, the first portion is coupled to the second portion via an interference fit.

In some embodiments, at least a portion of the first portion is disposed within the lumen defined by the sidewall of the second portion.

In some embodiments, the second portion is constructed of a multi-stranded wicking material. In some embodiments, the second portion is constructed of a yarn having wicking properties.

In some embodiments, the second portion has a configuration selected from a group consisting of a braided tube configuration, a long woven strip configuration and a stretched configuration.

In some embodiments, the second portion is constructed of a melt spun polypropylene with a high loading of barium sulphate.

In some embodiments, the second portion is constructed of a wicking material configured to deliver a fluid from the kidney to the bladder via capillarity.

In some embodiments, the ureteral stent includes a proximal retention structure configured to be disposed within the bladder of a patient. The proximal retention structure is coupled to the second portion of the elongate member.

In some embodiments, the ureteral stent includes a distal retention structure configured to be disposed within the kidney of the patent. The distal retention structure is coupled to the first portion of the elongate member.

In some embodiments, the second portion of the elongate member is substantially flexible.

In some embodiments, the first portion of the elongate member is substantially rigid.

In some embodiments, the second portion of the elongate member is more flexible than the first portion of the elongate member.

Although various embodiments have been described as having particular features and/or combinations of components, other embodiments are possible having a combination of any features and/or components from any of embodiments where appropriate.

What is claimed is:

1. A ureteral stent comprising: an elongate member having a first portion and a second portion, the second portion having a sidewall that defines a lumen, the first portion being coupled to the second portion, the first portion of the elongate member defining a lumen and at least a portion of the second portion of the elongate member being disposed within the lumen of the first portion, the second portion of the elongate member being more flexible than the first portion of the elongate member, the first portion configured to be disposed within a kidney of a patient, the sidewall of the second portion of the elongate member configured to deliver fluid from a first location of the sidewall of the second portion to a second location of the sidewall of the second portion via at least one of capillary action and wicking, the second portion of the elongate member configured to be disposed within at least one of a bladder of a patient and a ureter of the patient.

2. The ureteral stent of claim 1, wherein the second portion of the elongate member is constructed of a multi-stranded material.

3. The ureteral stent of claim 1, wherein the second portion of the elongate member is constructed of a yarn.

4. The ureteral stent of claim 1, wherein the second portion of the elongate member has a configuration selected from a group consisting of a braided tube configuration, a long woven strip configuration and a stretched configuration.

5. The ureteral stent of claim 1, wherein the second portion of the elongate member is constructed of a melt spun polypropylene with a high loading of barium sulphate.

6. The ureteral stent of claim 1, further comprising: a proximal retention structure configured to be disposed within the bladder of a patient, the proximal retention structure being coupled to the second portion of the elongate member.

7. The ureteral stent of claim 1, further comprising: a distal retention structure configured to be disposed within the kidney of the patent, the distal retention structure being coupled to the first portion of the elongate member.

8. The ureteral stent of claim 1, wherein the first portion is coupled to the second portion via an interference fit.

9. The ureteral stent of claim 1, wherein the second portion of the elongate member has a substantially solid tubular shape.

10. The ureteral stent of claim 1, wherein the second portion of the elongate member is substantially flexible.

11. The ureteral stent of claim 1, wherein the first portion of the elongate member is substantially rigid.

12. A ureteral stent comprising: an elongate member having a first portion and a second portion, the second portion having a sidewall that defines a lumen, the first portion being coupled to the second portion, the first portion of the elongate member defining a lumen and at least a portion of the second portion of the elongate member being disposed within the lumen of the first portion, the second portion of the elongate member being constructed of a multi-stranded material, the first portion configured to be disposed within a kidney of a patient, the sidewall of the second portion of the elongate member configured to deliver fluid from a first location of the sidewall of the second portion to a second location of the sidewall of the second portion via at least one of capillary action and wicking, the second portion of the elongate member configured to be disposed within at least one of a bladder of a patient and a ureter of the patient.

13. The ureteral stent of claim 12, wherein the second portion of the elongate member is constructed of a yarn.

14. The ureteral stent of claim 12, wherein the second portion of the elongate member has a configuration selected from a group consisting of a braided tube configuration, a long woven strip configuration and a stretched configuration.

15. The ureteral stent of claim 12, further comprising: a proximal retention structure configured to be disposed within the bladder of a patient, the proximal retention structure being coupled to the second portion of the elongate member.

16. The ureteral stent of claim 12, further comprising: a distal retention structure configured to be disposed within the kidney of the patent, the distal retention structure being coupled to the first portion of the elongate member.

17. The ureteral stent of claim 12, wherein the first portion is coupled to the second portion via an interference fit.

18. The ureteral stent of claim 12, wherein the second portion of the elongate member is substantially flexible.

19. The ureteral stent of claim 12, wherein the first portion of the elongate member is substantially rigid.

20. The ureteral stent of claim 12, wherein the second portion of the elongate member is more flexible than the first portion of the elongate member.

* * * * *